(12) United States Patent
Verleye et al.

(10) Patent No.: US 10,696,647 B2
(45) Date of Patent: Jun. 30, 2020

(54) PHARMACOLOGICAL TREATMENT OF OBSESSIVE-COMPULSIVE DISORDER

(71) Applicant: BIOCODEX, Gentilly (FR)

(72) Inventors: Marc Verleye, Remy (FR); Marie-Emmanuelle Le Guern, Compiegne (FR)

(73) Assignee: BIOCODEX, Gentilly (FR)

( * ) Notice: Subject to any disclaimer, the term of this patent is extended or adjusted under 35 U.S.C. 154(b) by 0 days.

(21) Appl. No.: 15/038,011

(22) PCT Filed: Nov. 20, 2014

(86) PCT No.: PCT/EP2014/075213
§ 371 (c)(1),
(2) Date: May 19, 2016

(87) PCT Pub. No.: WO2015/075155
PCT Pub. Date: May 28, 2015

(65) Prior Publication Data
US 2016/0289205 A1    Oct. 6, 2016

(30) Foreign Application Priority Data
Nov. 20, 2013  (EP) .................................. 13306586

(51) Int. Cl.
| | | |
|---|---|---|
| *C07D 317/54* | (2006.01) | |
| *A61K 31/36* | (2006.01) | |
| *A61K 31/55* | (2006.01) | |
| *A61K 31/343* | (2006.01) | |
| *A61K 31/138* | (2006.01) | |
| *A61K 31/519* | (2006.01) | |
| *A61K 31/135* | (2006.01) | |
| *A61K 31/4515* | (2006.01) | |
| *A61K 31/4525* | (2006.01) | |
| *A61K 31/15* | (2006.01) | |
| *A61K 45/06* | (2006.01) | |

(52) U.S. Cl.
CPC .......... *C07D 317/54* (2013.01); *A61K 31/135* (2013.01); *A61K 31/138* (2013.01); *A61K 31/15* (2013.01); *A61K 31/343* (2013.01); *A61K 31/36* (2013.01); *A61K 31/4515* (2013.01); *A61K 31/4525* (2013.01); *A61K 31/519* (2013.01); *A61K 31/55* (2013.01); *A61K 45/06* (2013.01)

(58) Field of Classification Search
CPC .............. A61K 2300/00; A61K 31/135; A61K 31/138; A61K 31/15; A61K 31/343; A61K 31/4515; A61K 31/4525; A61K 31/519; A61K 31/55; A61K 31/36; A61K 45/06; C07D 317/54
See application file for complete search history.

(56) References Cited

U.S. PATENT DOCUMENTS

| | | | | |
|---|---|---|---|---|
| 4,962,128 A | * | 10/1990 | Doogan | A61K 31/135 514/647 |
| 2010/0184806 A1 | | 7/2010 | Barlow et al. | |

FOREIGN PATENT DOCUMENTS

| | | |
|---|---|---|
| EP | 2201950 A1 | 6/2010 |
| FR | 2253503 A2 | 7/1975 |
| FR | 2253505 A2 | 7/1975 |
| WO | WO-01/64223 A1 | 9/2001 |
| WO | WO-2008/036678 A2 | 3/2008 |
| WO | WO-2008/036678 A3 | 3/2008 |
| WO | WO-2010/015029 A1 | 2/2010 |

OTHER PUBLICATIONS

I.F. Bloemen et al., "Obsessive compulsive symptoms in autism," Abstracts for Poster session III, European Psychiatry, 2008, vol. 23, p. S401.
Michael Kellner, "Drug treatment of obsessive-compulsive disorder," Dialogues in Clinical Neuroscience, 2010, vol. 12, No. 2, pp. 187-197.
Oulis Panagiotis et al., "The world journal of biological psychiatry: the official journal of the World Federation of Society of Biological Psychiatry," 2009, 1 page.
International Search Report and Written Opinion issued in International Patent Application PCT/EP2014/075213 dated Feb. 12, 2015.
European Search Report issued in European Patent Application No. 13306618 dated Feb. 24, 2014.
M. Poisson et al., "A New Type of Anticonvulsant, Stiripentol Pharmacological profile and neurochemical study," Arzneim-Forsch./Drug Res. 1984, vol. 34, pp. 199-204.
(Continued)

*Primary Examiner* — Sahar Javanmard
(74) *Attorney, Agent, or Firm* — Arent Fox LLP

(57) ABSTRACT

The present invention relates to a compound of the following formula (I):

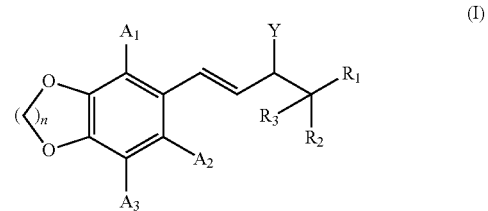

or a pharmaceutically acceptable salt thereof,
for use in the prevention or treatment of obsessions and/or compulsions in an individual.

17 Claims, 1 Drawing Sheet

(56) References Cited

OTHER PUBLICATIONS

Fujikawa et al., "Obsessive-Compulsive Behavior Induced by Levetiracetam," Journal of Child Neurology, 2014, accessed from https://journals.sagepub.com/doi/abs/10.1177/0883073814541471, pp. 1-4 (Abstract Provided).
Hirai et al., "Selective mutism and obsessive compulsive disorders associated with zonisamide," Seizure, 2002, vol. 11 pp. 468-470.
Ozkara et al., "Topiramate related obsessive-compulsive disorder," European Psychiatry, 2005, vol. 20, pp. 78-79.
Sherer et al., Mental Health Aspects of Developmental Disabilities, 2008, vol. 11, pp. 22-25, (1 page total, Abstract Provided).
Thuile et al., "Topiramate may induce obsessive-compulsive disorder," Psychiatry and Clinical Neurosciences, 2006, vol. 60, p. 394.
Astoin et al., "Action de nouveaux alcools α—éthyléniques sur le système nerveux central," Eur. J. Med. Chem.—Chimica Therapeutica, Jan.-Feb. 1978, pp. 41-47.
Gillham et al., "Concentration-effect relationships with carbamazepine and its epoxide on psychomotor and cognitive function in epileptic patients," Journal of Neurology and Psychiatry, vol. 51, pp. 929-933 (1988).
Tatum, IV et al., "Postmarketing Experience with Topiramate and Cognition," Epilepsia, vol. 42, No. 9, pp. 1134-1140 (2001).

* cited by examiner

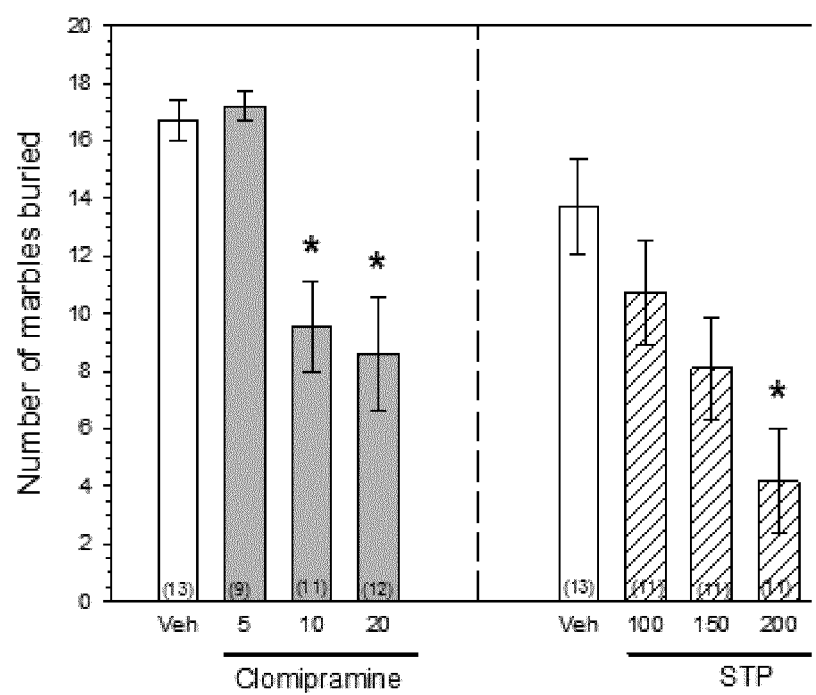

PHARMACOLOGICAL TREATMENT OF OBSESSIVE-COMPULSIVE DISORDER

CROSS REFERENCE TO RELATED APPLICATION

This application is a 35 U.S.C 371 National Phase of PCT Application No. PCT/EP2014/075213 filed Nov. 20, 2014 which claims priority to European Application No. 13306586.2 filed Nov. 20, 2013, the disclosure of these prior applications are hereby incorporated in their entirety by reference.

FIELD OF THE INVENTION

The present invention relates to methods and compositions for treating obsessive-compulsive disorder.

BACKGROUND OF THE INVENTION

Obsessive-compulsive disorder (OCD) is characterized by recurrent and persistent thoughts, impulses or images (obsessions) and/or repetitive behaviors or mental acts that the person feels driven to perform (compulsions), e.g. doubting, checking and washing. The lifetime prevalence of OCD is 1-3% in the general population. Like many psychiatric disorders, OCD is likely a heterogeneous disorder comprised of several subtypes with distinct genetic and environmental risk factors and pathophysiological mechanisms.

The first line therapy of OCD includes selective serotonin reuptake inhibitors (SSRI), such as escitalopram, fluvoxamine, fluoxetine, paroxetine, and sertraline, as well as clomipramine, a tricyclic antidepressant (TCA), which inhibits serotonin reuptake (Kellner (2010) Dialogues Clin Neurosci. 12:187-197).

However, clomipramine is less well tolerated than the SSRIs. Besides, about 40% to 60% of the patients do not respond sufficiently to oral serotonergic antidepressants. Accordingly, there is a need for other drugs to manage OCD (Kellner (2010) Dialogues Clin Neurosci. 12:187-197).

Stiripentol (Diacomit, 1-penten-3-ol-(1,3-benzodioxol)-4,4-dimethyl or 4-dimethyl-1-[3,4-methylenedioxy-3,4)-phenyl]-1-penten-3-ol) is a racemic allylic alcohol that is structurally unrelated to other antiepileptic drugs.

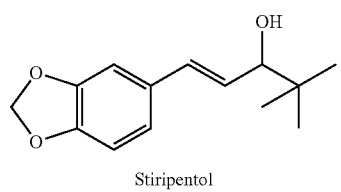 [SMILES: CC(C)(C)C(O)/C=C/c1ccc2c(c1)OCO2]

Stiripentol

Stiripentol has shown anticonvulsant activity in several animal models but its spectrum of clinical activity is relatively narrow. The efficacy of Stiripentol, as an add-on therapy to valproate and clobazam, in controlling epilepsy seizures in children presenting with Dravet syndrome, was demonstrated in two randomized, double-blind, placebo-controlled studies. The primary efficacy endpoint for both studies was responder rate. A responder was defined as a patient who experienced a ≥50% decrease in the frequency of generalized clonic or tonic-clonic seizures during the double-blind treatment period compared to baseline (Chiron (2000) Lancet 356:1638). Stiripentol was granted a European Marketing Authorisation for this indication.

SUMMARY OF THE INVENTION

The present invention arises from the unexpected finding, by the inventors, that stiripentol is useful in a rat model of obsessive compulsive disorder.

The present invention thus relates to a compound of the following formula (I):

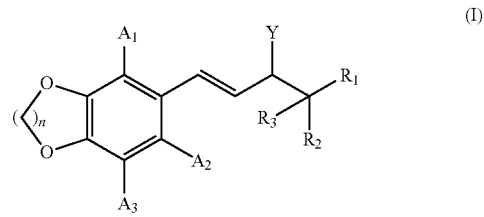

wherein:
  n represents 1 or 2,
  $A_1$, $A_2$ and $A_3$, which may be identical or different, represent a hydrogen atom, a halogen atom or a linear or branched alkyl group having from 1 to 4 carbon atoms,
  $R_1$, $R_2$ and $R_3$ represent independently a hydrogen atom or a linear or branched alkyl group having from 1 to 4 carbon atoms, and
  Y represents —OH, =O or —SH;
or a pharmaceutically acceptable salt thereof,
for use in the prevention or treatment of obsessions and/or compulsions in an individual.

The present invention also relates to a method for the prevention or treatment of obsessions and/or compulsions in an individual, comprising administering the individual a prophylactically or therapeutically effective quantity of at least one compound of formula (I) as defined above.

The present invention also relates to the use of at least one compound of formula (I) as defined above for the manufacture of a medicament intended for the prevention or treatment of obsessions and/or compulsions in an individual.

In an embodiment of the compound or pharmaceutically acceptable salt thereof for its use as defined above, the method as defined above or the use as defined above, the compound of formula (I) is in combination, or is combined, with at least one additional compound intended for preventing or treating obsessions and/or compulsions.

In another embodiment of the compound or pharmaceutically acceptable salt thereof for its use as defined above, the method as defined above or the use as defined above, the compound of formula (I) is not in combination, or combined, with another prophylactically or therapeutically active compound, such as a PDE4 inhibitor, a neurokinin-1 receptor antagonist, an A1 adenosine receptor agonist, an alpha-2 adrenoreceptor agonist, an A2A adenosine receptor agonist, a PPARγ agonist, fluvoxamine, risperidone, or a lithium salt.

The present invention also relates to a pharmaceutical composition, comprising as active substances at least one compound of formula (I) as defined above, or a pharmaceutically acceptable salt thereof, for use in the prevention or treatment of obsessions and/or compulsions in an individual.

In an embodiment of the invention, the pharmaceutical composition for use as defined above further comprises at least one additional compound intended for preventing or treating obsessions and/or compulsions.

The present invention also relates to a pharmaceutical composition comprising as active substances, at least one compound of formula (I) as defined above, or a pharmaceutically acceptable salt thereof, and at least one additional compound intended for preventing or treating obsessions and/or compulsions in particular selected from the group constituted of selective serotonin reuptake inhibitors (SSRI), such as escitalopram, fluvoxamine, fluoxetine, paroxetine, and sertraline, tricyclic antidepressants (TCA), such as clomipramine, and neuroleptics, such as haloperidol and risperidone, optionally in association with a pharmaceutically acceptable vehicle.

The present invention also relates to products containing:
at least one compound of formula (I) as defined above, or a pharmaceutically acceptable salt thereof, and
at least one additional compound intended for preventing or treating obsessions and/or compulsions,
as a combined preparation for simultaneous, separate or sequential use in the prevention or treatment of obsessions and/or compulsions.

DESCRIPTION OF THE INVENTION

Preferably, the above-defined compound of formula (I) is represented by the following formula (II):

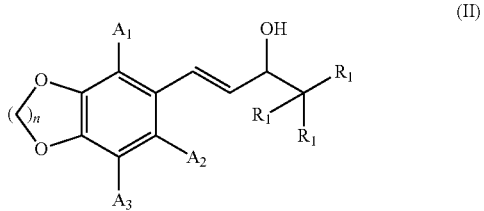

(II)

in which n, $A_1$, $A_2$, $A_3$ and $R_1$ are as defined above.

More preferably the above-defined compound of formula (I) or (II) is represented by the following formula (III), i.e. is stiripentol:

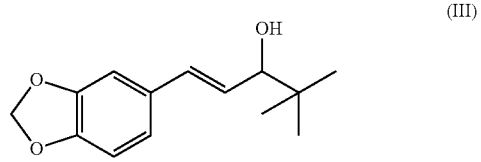 [SMILES: CC(C)(C)C(O)/C=C/c1ccc2c(c1)OCO2]

(III)

Preferred alkyl groups according to the invention encompass the methyl, ethyl, n-propyl, isopropyl, n-butyl, s-butyl and t-butyl groups. The Cl, I, Br or F atoms are preferred halogen atoms according to the invention.

French patent FR 2 173 691, which is incorporated herein by reference, describes the synthesis of stiripentol, in particular starting from methylenedioxy-3,4-phenyl)-1-dimethyl-4,4-penten-1-on-3. It is well within the ordinary skills of one of skill in the art to synthesize the other compounds of formula (I) from this teaching.

As will be clear to one of skill in the art, the above-defined formulas (I), (II), and (III) represent either the various stereoisomers encompassed by these formulas or mixtures thereof, in particular racemic mixtures thereof.

Thus, the compound of formula (III) can be a compound of formula (IIIa) a compound of formula (IIIb), or a mixture of a compound of formula (IIIa) and a compound of formula (IIIb), in particular the racemic mixture thereof.

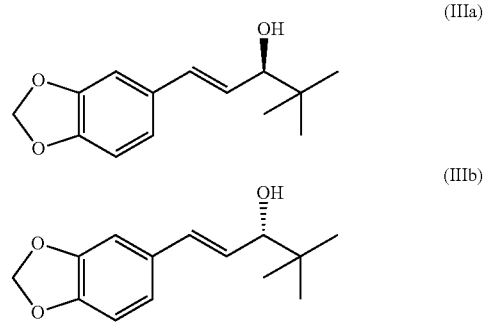

Obsessions, in particular obsessive thoughts, impulses, ideas or images, and compulsions, also named compulsive behaviour or compulsive acts, are well known to one of skill in the art.

By way of example, obsessions are persistent ideas, thoughts, impulses, or images that are experienced as intrusive and inappropriate and that cause marked anxiety or distress. By way of example also, compulsions are repetitive behaviors (e.g. hand washing, ordering, checking) or mental acts (e.g. praying, counting, repeating words silently) the goal of which is to prevent or reduce anxiety or distress, not to provide pleasure or gratification.

Preferably, obsessive-compulsive disorder (OCD) has to be prevented or treated in the above-defined individual.

Obsessive-compulsive disorder (OCD) is well known to one of skill in the art.

By way of example, the fifth edition of the Diagnostic and Statistical Manual of Mental Disorders (DSM-5™) (American Psychiatric Publishing, 2013) defines the following criteria for OCD (coded 300.3):

A. Presence of obsessions, compulsions, or both:
Obsessions are as defined by (1), and (2):
1. Recurrent and persistent thoughts, urges, or images that are experienced, at some time during the disturbance, as intrusive and unwanted, and that in most individuals cause marked anxiety or distress.
2. The individual attempts to ignore or suppress such thoughts, urges, or images, or to neutralize them with some other thought or action (i.e. by performing a compulsion).
Compulsions as defined by (1) and (2):
1. Repetitive behaviors (e.g. hand washing, ordering, checking) or mental acts (e.g. praying, counting, repeating words silently) that the individual feels driven to perform in response to an obsession, or according to rules that must be applied rigidly.
2. The behaviors or mental acts are aimed at preventing or reducing anxiety or distress, or preventing some dreaded event or situation; however, these behaviors or mental acts either are not connected in a realistic way with what they are designed to neutralize or prevent, or are clearly excessive.
Note: Young children may not be able to articulate the aims of these behaviors or mental acts.
B. The obsessions or compulsions are time-consuming (e.g. take more than 1 hour per day), or cause clinically significant distress or impairment in social occupational, or other important areas of functioning.

C. The obsessive-compulsive symptoms are not attributable to the physiological effects of a substance (e.g. a drug of abuse, a medication) or another medical condition.

D. The disturbance is not better explained by the symptoms of another mental disorder (e.g. excessive worries, as in generalized anxiety disorder; preoccupation with appearance, as in body dysmorphic disorder; difficulty discarding or parting with possessions, as in hoarding disorder; hair pulling, as in trichotillomania [hair-pulling disorder]; skin picking, as in excoriation [skin-picking] disorder; stereotypes, as in stereotypic movement disorder; ritualized eating behavior, as in eating disorders; preoccupation with substances or gambling, as in substance-related and addictive disorders; preoccupation with having an illness, as in illness anxiety disorder; sexual urges or fantasies, as in paraphilic disorders; impulses, as in disruptive, impulse-control, and conduct disorders; guilty ruminations, as in major depressive disorder; thought insertion or delusional preoccupations, as in schizophrenia spectrum and other psychotic disorders; or repetitive patterns of behavior, as in autism spectrum disorder).

By way of example, the tenth version of the international classification of diseases (ICD-10) established by the World Health Organization (WHO) regarding the classification of mental and behavioural disorders defines the following criteria for OCD (coded F42):

A. Either obsessions or compulsions (or both), present on most days for a period of at least two weeks.

B. Obsessions (thoughts, ideas or images) and compulsions (acts) share the following features, all of which must be present:
  (1) They are acknowledged as originating in the mind of the patient, and are not imposed by outside persons or influences.
  (2) They are repetitive and unpleasant, and at least one obsession or compulsion must be present that is acknowledged as excessive or unreasonable.
  (3) The subject tries to resist them (but if very long-standing, resistance to some obsessions or compulsions may be minimal). At least one obsession or compulsion must be present which is unsuccessfully resisted.
  (4) Carrying out the obsessive thought or compulsive act is not in itself pleasurable. (This should be distinguished from the temporary relief of tension or anxiety).

C. The obsessions or compulsions cause distress or interfere with the subject's social or individual functioning, usually by wasting time.

D. Most commonly used exclusion criteria: not due to other mental disorders, such as schizophrenia and related disorders (F2), or mood [affective] disorders (F3).

The diagnosis may be specified by the following four character codes:

F42.0 Predominantly obsessional thoughts and ruminations
F42.1 Predominantly compulsive acts
F42.2 Mixed obsessional thoughts and acts
F42.8 Other obsessive-compulsive disorders
F42.9 Obsessive-compulsive disorder, unspecified Preferably, the individual has undergone functional neurosurgery, in particular in view of treating or alleviating obsessions and/or compulsions, more particularly in view of treating obsessive compulsive disorder (OCD). Preferably, the individual is not suffering from autism or autism spectrum disorder (ASD).

Preferably, the compound of formula (I) as defined above or the pharmaceutically acceptable salt thereof, is to be administered at a unit dose of from 100 mg to 1000 mg or of from 5 mg/kg to 100 mg/kg. Preferably also, the compound of formula (I) as defined above or the pharmaceutically acceptable salt thereof is to be administered with a dosage regimen of from 10 mg/kg/d to 200 mg/kg/d. Preferably, the compound of formula (I) as defined above or the pharmaceutically acceptable salt thereof is not administered in a sub-therapeutic amount for mood stabilization treatment of epilepsy or epileptic symptoms.

Preferably, the compound of formula (I) as defined above or the pharmaceutically acceptable salt thereof, the pharmaceutical composition for use as defined above, the pharmaceutical composition as defined above or the medicament as defined above, is in a form suitable for administration by the oral or rectal route. Preferably also, the compound of formula (I) as defined above or the pharmaceutically acceptable salt thereof, the pharmaceutical composition as defined above or the medicament as defined above, is in the form of a powder, sachets, tablets, capsules or suppositories.

As intended herein, the expression "additional compound intended for obsessions and/or compulsions" relates to any compound intended to alleviate one or more of the symptoms of or to treat or prevent obsessions and/or compulsions, in particular obsessive-compulsive disorder. Preferably, the at least one additional compound intended for preventing or treating obsessions and/or compulsions is selected from the group constituted of selective serotonin reuptake inhibitors (SSRI), such as escitalopram, fluvoxamine, fluoxetine, paroxetine, and sertraline, tricyclic antidepressants (TCA), such as clomipramine, and neuroleptics, such as haloperidol and risperidone.

As intended herein "combined" or "in combination" means that the compound of formula (I) as defined above or the pharmaceutically acceptable salt thereof, in particular stiripentol, are administered at the same time than the additional compound, either together, i.e. at the same administration site, or separately, or at different times, provided that the time period during which the compound of formula (I) as defined above or the pharmaceutically acceptable salt thereof exerts its pharmacological effects on the individual and the time period during which the additional compound exerts its pharmacological effects on the individual, at least partially intersect.

DESCRIPTION OF THE FIGURE

FIG. 1 represents the influence of stiripentol (STP) and clomipramine administered i.p. at different doses (horizontal axis, in mg/kg) on the marble-burying behavior in mice (vertical axis). Each bar represent the mean±sem. The number of animals used appears in brackets. *$p<0.05$ compared to vehicle group (Veh) (ANOVA or Kruskall Wallis test followed by Dunnett's test or Dunn's method respectively).

EXAMPLE

Marble-burying behavior in the rodent is considered to be a model of obsessive-compulsive disorder (OCD) and is commonly used to assess the activity of candidate compounds in the prevention or treatment of OCD (Ishimaru et al. (1995) *Jpn. J. Pharmacol.* 68:65-70; Gaikwad & Parle (2010) *Asian Journal of Pharmaceutical and Clinical Research* 3:101-103; Prajapati et al. (2011) *Pharmacognosy Res.* 3:62-66). Accordingly, the effects of stiripentol and clomipramine, chosen as positive reference, on marble-burying behavior were investigated in mice. In addition, because the motor behavior can interfere with the burying behavior, the effects of stripentol in the rota rod test and spontaneous locomotion have been also evaluated.

1 METHODS

1.1 Animals

Six-week old NMRI mice (30-32 g) were purchased from Janvier breeding (Le Genest-St Isle; France). Mice were housed ten per translucent polypropylene cage (internal dimensions; 37.5 cm×37.5 cm×180 cm, L×W×H) under standard laboratory conditions (22±2° C., 12-h light/dark cycle, lights on at 7:00 AM) with food (AO4, SAFE, France) and tap water available ad libitum. No less than one week of rest followed their arrival. All animal procedures were carried out in accordance with the European Community council directive of 24 of Nov. 1986 (86/609/EEC) for the care and use of laboratory animals and the French government guidelines (authorization C60-159-04—December, 2009).

1.2 General Testing Conditions and Treatments.

Mice were habituated to the testing room at least 60 min before any behavioural evaluation. All tests took place between 9:00 AM and 3:00 PM unless otherwise stated. The behavioural tests were performed by different well-trained experimenters who were kept unaware of the treatment administered. All experiments were performed in a randomized manner. Stiripentol (100-200 mg/kg) and clomipramine (5-20 mg/kg) were given intra-peritoneously (i.p.) 60 and 30 min respectively before testing.

1.3 Marble-Burying Behavior

The marble-burying behavior of mice was conducted according to the methodology of Njung'e and Handley (1991) *Pharmacol Biochem Behav* 1991; 38: 63-67. Briefly, each mouse was placed individually in a polycarbonate cage (Type S-River; 26.5×16×14 cm height) containing 20 clean glass marbles of diameter 1.5 cm evenly spaced on 5 cm deep sawdust. The cage-lid was a metal grid. No food or water was present. The marbles were cleaned with an alcohol solution (10%; v/v) between each animal. The number of marbles at least ⅔ buried was counted 30 min later.

1.4 Spontaneous Locomotor Activity

Testing occurred in a quiet room under a light level of approximately 400 lux. The motor activity cages (type S; River; polycarbonate; 26.5×16×14 cm height) were made of clear plastic, changed between each animal, and containing a minimum amount of sawdust. Locomotor activity and rearing were measured by vibrations analysis and the interruption of infra-red beams respectively (ActiV-Meter; Software BIO-ACTIV; Bioseb-Vitrolles-France). The distance travelled (in cm) and the number of rearings were measured for 30 min.

1.5 Rotarod Test

The rotarod test was performed in accordance with the teachings of Kohara et al. (2005) *J Pharmacol Exp Ther* 2005; 315: 163-169. Briefly, the rotarod consists of a 3-cm-diameter rod rotating at a fixed speed of 16 revolutions per minute (model 7600; Ugo Basile, Comerio Italy), which can be used to assess motor performance. Mice were trained to walk on the rotarod until they could complete three consecutive 120-s sessions without falling off. Mice that show a 120 s performance time were selected for drug evaluation. Animals were then given i.p. either vehicle or various doses of either compound before being placed on the rotarod. In the drug evaluation session, rotarod performance time was measured three times, up to 120 s, and the mean was adopted as the performance time for each animal. The performance of the animals on the rota rod requires skill and motor coordination.

1.6 Drugs

Stiripentol (batch 167, Biocodex, France) was suspended in a saline solution of 5% tween 80 (v/v) whereas clomipramine hydrochloride (Sigma-France) was dissolved in 0.9% saline. These compounds were administered under a volume of 0.1 ml/10 g of body weight. Control animals received an equivalent volume of vehicle.

1.7 Statistical Analysis

All data are expressed as mean±SEM. The number of marble buried, locomotor activity and the time spent on the rot rod were analyzed by one-way analyse of variance (ANOVA) or the Kruskall Wallis procedure followed post-hoc by the Dunnett's test or Dunn's method respectively to locate the differences between the treated groups and the vehicle group. Differences were considered statistically significant when $p<0.05$. Statistical tests were run using SigmaStat v3.5 (SPSS, inc, Chicago, Ill., USA).

2 RESULTS

As shown in FIG. 1, stiripentol dose-dependently decreased the number of marbles buried $[F(3.42)=5.425; p=0.003]$ and significance was reached for the dose of 200 mg/kg. Likewise, clomipramine significantly reduced the number of marbles buried $[H(3)=20.412; p<0.001]$ and significance was reached at the doses of 10 and 20 mg/kg.

Besides, stiripentol did not significantly modify the distance travelled up to 200 mg/kg of stiripentol. Similarly, stiripentol did not significantly impair the number of rearings up to 200 mg/kg. In addition, doses of stiripentol up to 200 mg/kg were without any significant effect on the time spent on the rot rod.

3 DISCUSSION

Marble-burying behaviour of mice is considered as the marker index of compulsive behaviour, which is characteristically evident in OCD. This behaviour is an unconditioned species-specific defensive reaction in rodents, which is not associated with physical danger, and does not habituate upon repeated testing. The major finding of the present study is that stiripentol reduced marble burying behaviour. A similar reduction in the number of marbles buried was observed in mice treated with clomipramine, chosen as reference compound and clinically used as anti-compulsive agent.

It is noteworthy that these "anti-compulsive-like" effects of stiripentol could be theoretically compromised by sedative-like or ataxic actions. However, by comparing marble burying scores with locomotor activity and rota rod measures, the inventors have shown that stiripentol inhibited marble burying at doses that did not affect motor activities. Similarly, it has been shown that the anti-compulsive effects of clomipramine were specific and unrelated to general motor effects in the mouse.

4. CONCLUSION

In the OCD mouse model of marble-burial, stiripentol reduced the number of marble buried in the mouse without affecting locomotor activity.

The invention claimed is:

1. A method for the treatment of obsessions and/or compulsions in an individual, comprising administering to the individual a therapeutically effective quantity of at least one compound of the following formula (III):

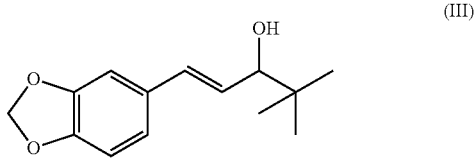 [SMILES: CC(C)(C)C(O)/C=C/c1ccc2c(c1)OCO2]

or the pharmaceutically acceptable salt thereof,
at a dose which treats obsessions and/or compulsions, wherein the compound or pharmaceutically acceptable salt thereof is administered at a dose regimen of from 10 mg/kg/d to 200 mg/kg/d.

2. The method of claim 1, for the treatment of obsessive-compulsive disorder (OCD).

3. The method of claim 1, wherein the compound or pharmaceutically acceptable salt thereof is in a form suitable for administration by the oral or rectal route.

4. The method of claim 1, wherein the compound or pharmaceutically acceptable salt thereof is in the form of a powder, sachets, tablets, capsules or suppositories.

5. The method of claim 1, wherein the compound or pharmaceutically acceptable salt thereof is in combination with at least one additional compound intended for treating obsessions and/or compulsions.

6. The method of claim 1, wherein the compound or pharmaceutically acceptable salt thereof is in combination with at least one additional compound intended for treating obsessions and/or compulsions comprising selective serotonin reuptake inhibitors (SSRI), tricyclic antidepressants (TCA) or neuroleptics.

7. The method of claim 1, wherein the compound or pharmaceutically acceptable salt thereof is in combination with at least one additional compound intended for treating obsessions and/or compulsions comprising escitalopram, fluvoxamine, fluoxetine, paroxetine, sertraline, clomipramine, haloperidol or risperidone.

8. A method for the treatment of obsessions and/or compulsions in an individual, comprising administering to the individual a therapeutically effective quantity of at least one compound of the following formula (III):

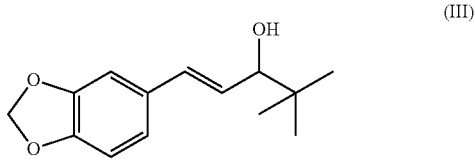 [SMILES: CC(C)(C)C(O)/C=C/c1ccc2c(c1)OCO2]

or the pharmaceutically acceptable salt thereof, wherein the compound of formula (III) or the pharmaceutically acceptable is administered at a unit dose which is not a sub-therapeutic amount for mood stabilization treatment of epilepsy or epileptic symptoms, wherein the compound or pharmaceutically acceptable salt thereof is administered at a dose regimen of from 10 mg/kg/d to 200 mg/kg/d.

9. The method of claim 8, for the treatment of obsessive-compulsive disorder (OCD).

10. The method of claim 8, wherein the compound or pharmaceutically acceptable salt thereof is in a form suitable for administration by the oral or rectal route.

11. The method of claim 8, wherein the compound or pharmaceutically acceptable salt thereof is in the form of a powder, sachets, tablets, capsules or suppositories.

12. The method of claim 8, wherein the compound or pharmaceutically acceptable salt thereof is in combination with at least one additional compound intended for preventing or treating obsessions and/or compulsions.

13. The method of claim 8, wherein the compound or pharmaceutically acceptable salt thereof is in combination with at least one additional compound intended for treating obsessions and/or compulsions comprising selective serotonin reuptake inhibitors (SSRI), tricyclic antidepressants (TCA) or neuroleptics.

14. The method of claim 8, wherein the compound or pharmaceutically acceptable salt thereof is in combination with at least one additional compound intended for treating obsessions and/or compulsions comprising escitalopram, fluvoxamine, fluoxetine, paroxetine, sertraline, clomipramine, haloperidol or risperidone.

15. The method of claim 1, wherein the compound or pharmaceutically acceptable salt thereof is administered at a unit dose which is not a sub-therapeutic amount for mood stabilization treatment of epilepsy or epileptic syndrome.

16. A method for the treatment of obsessions and/or compulsions, comprising administering to the individual a therapeutically effective quantity of at least one compound of the following formula (III):

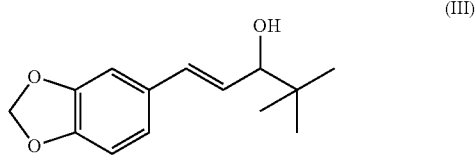 [SMILES: CC(C)(C)C(O)/C=C/c1ccc2c(c1)OCO2]

or a pharmaceutically acceptable slat thereof, at a dose which treats obsessions and/or compulsions, wherein the compound or pharmaceutically acceptable salt thereof is administered at a dose regimen of from 10 mg/kg/d to 200 mg/kg/d.

17. A method for the treatment of obsessions and/or compulsions involving repetitive behavior in an individual, comprising administering to the individual a therapeutically effective quantity of at least one compound of the following formula (III):

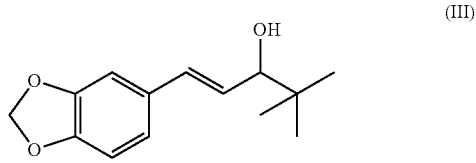 [SMILES: CC(C)(C)C(O)/C=C/c1ccc2c(c1)OCO2]

or a pharmaceutically acceptable salt thereof, wherein the compound or pharmaceutically acceptable salt thereof is administered at a dose regimen of from 10 mg/kg/d to 200 mg/kg/d.

* * * * *